United States Patent [19]

Tapper

[11] Patent Number: 5,224,927
[45] Date of Patent: Jul. 6, 1993

[54] IONTOPHORETIC TREATMENT SYSTEM

[76] Inventor: Robert Tapper, 1935 Armacost Ave., Los Angeles, Calif. 90025

[21] Appl. No.: 607,874

[22] Filed: Nov. 1, 1990

[51] Int. Cl.$^5$ ............................................. A61N 1/30
[52] U.S. Cl. .................................... 604/20; 128/803; 128/898
[58] Field of Search ................... 604/20, 783; 128/798, 128/802, 803

[56] References Cited

U.S. PATENT DOCUMENTS

| | | | |
|---|---|---|---|
| 3,054,405 | 9/1962 | Tapper | 604/20 |
| 4,340,047 | 7/1982 | Tapper et al. | 604/20 |
| 4,406,658 | 9/1983 | Lattin et al. | 604/20 |
| 4,640,689 | 2/1987 | Sibalis | 604/20 |
| 4,702,732 | 10/1987 | Powers et al. | 604/20 |
| 4,786,277 | 11/1988 | Powers et al. | 604/20 |
| 4,808,152 | 2/1989 | Sibalis | 604/20 |
| 4,931,046 | 6/1990 | Newman | 604/20 |
| 4,963,367 | 10/1990 | Ecanow | 604/892.1 |
| 4,973,303 | 11/1990 | Johnson et al. | 604/20 |
| 5,006,108 | 4/1991 | LaPrade | 604/20 |
| 5,013,293 | 5/1991 | Sibalis | 604/20 |
| 5,019,034 | 5/1991 | Weaver et al. | 604/20 |
| 5,023,085 | 6/1991 | Francover et al. | 604/20 |
| 5,047,007 | 9/1991 | McNichols et al. | 604/20 |

FOREIGN PATENT DOCUMENTS 2206493 1/1989 United Kingdom .

OTHER PUBLICATIONS

Research Disclosure No. 29504 on Method for Multiple Drug Delivery via Iontophoresis-Lattin et al.
Research Disclosure No. 29520 on Method to Control Delivery of Uncharged Drugs via Iontophoresis-Lattin.
Journal of Pharmaceutical Sciences, vol. 67, No. 10, Oct. 1989, Conductivity of Drugs Used for Iontophoresis-Gangarosa et al.
Controlled Release Society, Inc., Important Parameters Affecting Iontophoretic Transdermal Delivery of Insulin-Sun et al.
Skin Permeability-9. Iontophoresis-Shaefer et al.
Clayton's Electrotherapy and Actinotherapy-Scott.
Studies on Iontophoresis-Experimental Studies on the Causes and Prevention of Iontophoretic Burns-Molitor.
Excerpt from the Federal Register, vol. 44, No. 168. Electrotherapy-Wolf.
Medical Research Engineering, Oct.-Nov. 1971, Low Voltage, Direct Current Plethysmograph Burns-Leeming et al.
JAMA, Nov. 30, 1970. vol. 214, No. 9, Low-Voltage, Direct-Current Burns-Leeming et al.
A Manual of Electrotherapy, The Direct Current and Ion Transfer-Watkins.
Journal of Pharmaceutical Sciences, vol. 78, No. 5, May 1989, Ion-tophoretic Delivery of Model Inorganic & Drug Ions-Lattin et al.
Journal of Controlled Release, 11 (1990) 123-125, in vitro and in vivo Evaluation of Transdermal Iontophoretic Delivery of Hydromorphone-Lattin et al.
The Journal of Orthopaedic & Sports Physical Therapy, Introduction of Antiinflammatory Drugs by Iontophoresis: Double Blind Study-Bertolucci.
Pediatrics 48:(5)831-832, Nov. 1971, Low Voltage Skin Burns-Jarvis et al.

(List continued on next page.)

Primary Examiner—Stephen C. Pellegrino
Assistant Examiner—Michael Rafa
Attorney, Agent, or Firm—Fulwider, Patton, Lee & Utecht

[57] ABSTRACT

A method and apparatus for applying iontophoretic treatment to a biological subject wherein electrical treatment current between a pair of electrodes is periodically reversed at very low frequencies, substantially in the range of approximately 0.0027 Hz to approximately 10 Hz, to mitigate tissue damage, enable long term dosimetry with single and multiple drugs of any polarity and at higher concentrations, and eliminate the need for buffering agents and the like, all in a relatively simple, economical and compact physical packaging configuration. The system delivers treatment substances with large and/or small molecular size and weight and can be adjusted to control pH at the delivery site. A method of lowering resistance and enhancing permeability at the delivery site is also provided.

19 Claims, 4 Drawing Sheets

OTHER PUBLICATIONS

Cutis, vol. 26, Aug. 1980, Treatment of Hyperhidrosis by Tap Water Iontophoresis–Levit.

Arch Derm, vol. 98, Nov. 1968, Simple Device for Treatment of Hyperhidrosis by Iontophoresis–Levit.

British Journal of Dermatology (1977) 96, 189, Tap Water Iontophoresis in Palmo-Plantar Hyperhidrosis–Shrivastava et al.

Mechanism of Action of Iontophoresis in the Treatment of Palmar Hyperhidrosis–Hill et al.

Poldine Iontophoresis in the Treatment of Palmar and Plantar Hyperhidrosis–Hill.

American Journal of Physical Medicine, vol. 31, Jun. 1952, No. 3, The Treatment of Hyperhidrosis of Hands and Feet with Constant Current–Bouman et al.

Phoresor Phorum, Choosing the Right Drugs.

Iontophoretic Delivery of Drugs: Fundamentals, Developments and Biomedical Applications–Banga et al.

Ionic Medication in Dermatology–Shaffer.

Transdermal Drug Delivery–Burnette.

Journal of the APTA, vol. 43, No. 8, The Iontophoresis of $C_{21}$ Esterfied Glucocorticoids: Preliminary Report–Murray et al.

Iontophoretic Transport of a Homologous Series of Ionized & Nonionized Model Compounds: Influence of Hydrophobicity & Mechanistic Interpretation–Del Terzo et al.

Increased Penetration of Nonelectrolytes into Mouse Skin During Iontophoretic Water Transport (Iontohydrokinesis)–Gangarosa et al.

Therapeutic Electricity and Ultraviolet Radiation–Licht et al.

Electrophoretic Therapy–Harpuder.

Transdermal Drug Delivery Development Issues and Research Initiatives–Burnette et al.

Penetration of Surface Tissues with Copper by Iontophoresis–Penetration with Organic and Inorganic Copper Salts and the Use of Detergents in Iontophoresis–Pereyra.

Soap/Cosmetics/Chemical Specialties, Amphoteric Surfactants–A Structure Function Study–Bilbo et al.

IONTOPHORETIC TREATMENT SYSTEM

BACKGROUND OF THE INVENTION

This invention relates generally to improvements in methods and apparatus for effecting an electrotherapeutic treatment on a biological subject, such as iontophoretic delivery of medicaments and, more particularly, to a new and improved system for the application of an iontophoretic treatment topically to the skin of a human body.

Around the turn of the century there was disclosed a plethora of electrode types for applying "electric treatments" to the human body. The electrodes were normally placed upon the body in relation to the position of the organ to be treated. Such "electric treatments" encompassed a wide range of applications. For example, galvanic (direct current) treatments have been popular in the past for their polar effects on ionized molecules, causing the ionized molecules to be driven through the skin, usually superficially. This phenomenon is known as iontophoresis or ion transfer, and it has been employed for the introduction of medicaments or even simply moisture, into the skin of a patient.

More specifically, and by way of example, some ions of zinc and copper can be employed in the treatment of various skin infections, and chlorine ions have been employed for the loosening of superficial scars. Further, vasodilating drugs can be used in rheumatic and peripheral vascular affections, and skin anesthesia can be produced by iontophoresis of local anesthetic drugs. Moreover, iontophoretic administration of drugs typically avoids the gastrointestinal side effects sometimes associated with direct ingestion of such drugs.

Although the aforementioned iontophoretic treatments have been found to be effective, they are also known to be accompanied by a number of undesirable side effects, such as the occurrence of skin injury in the form of iontophoretic burns and irritation in the treated area, as well as the formation of undesirable vesicles and bulla, on the skin in the treated area. Various complicated or compromised methods for preventing these iontophoretic burns have been developed. However, such methods and apparatus have generally been found not to be adequately effective for preventing irritation and the formation of vesicles or bulla on the skin in the treated area. Consequently, iontophoretic treatments have usually been limited to relatively low electrical currents and relatively short periods of administration of, typically, twenty minutes or less.

Iontophoretic drug delivery systems of the prior art have also been primarily limited to delivering a drug of only a single polarity at a time to a given area, at relatively low concentrations, and have not been suitable for simultaneous delivery of multiple drugs. Furthermore, there were virtually no satisfactory iontophoretic devices which were relatively simple, economical, compact, portable and capable of safe, long term delivery over several days, once applied to the patient and placed into operation. Attempts to meet these needs have involved rather complex buffering, electrical or other compensatory systems which have not proven entirely practical or satisfactory.

In addition to the foregoing difficulties, iontophoretic systems of the past have not proven effective in the administration of drugs embodying relatively large and/or heavy molecular structures. Moreover, drug formulations intended for iontophoretic therapeutic drug delivery have oftentimes required buffering agents for pH control. Control of pH at the delivery site of the therapeutic drug has been essentially unknown. Furthermore, difficulties in obtaining sufficiently high rates of infusion, due to relatively high electrical resistance and/or poor permeability at the delivery site, have also been encountered with iontophoretic systems.

The aforementioned difficulties and undesirable side effects of iontophoretic treatment have resulted in a sometimes less than enthusiastic reception of iontophoretic techniques by the medical community, in spite of the potentially great and varied advantages to be realized through their use and development.

Hence, those concerned with development and use of iontophoretic systems in the medical field have long recognized the need for a convenient and effective apparatus and method for preventing burns, irritation and the formation of vesicles and bulla on the skin in an area subjected to an iontophoretic treatment over extended periods of continuous treatment, for systems which can be physically packaged in a relatively simple, economical and compact configuration, can deliver therapeutic drugs at a relatively high rate and at higher concentrations, without the need for buffering agents and the like, which are capable of delivering large molecular substances such as insulin and the like, can deliver a plurality of drugs simultaneously in a relatively simple manner without matching drug polarity, can be used to lower resistance and increase permeability, and can be used to reliably control pH at the drug administration site. As will become apparent from the ensuing discussion, the present invention clearly fulfills all of these needs and more.

SUMMARY OF THE INVENTION

Briefly, and in general terms, the present invention provides a method and apparatus for applying electrical energy topically to a suitable surface of a biological subject, such as the skin of a human body, particularly for the long term administration of medicaments and the like or for other electrotherapeutic treatment, and by which the aforementioned deficiencies and undesired side effects are greatly minimized and may be eliminated. Moreover, the system of the present invention is relatively inexpensive to manufacture, can be physically packaged in a completely self-contained, relatively simple and compact configuration, trouble free and reliable in use, is capable of higher drug administration rates and drug concentrations, can deliver multiple drugs simultaneously in a simple manner, can control pH at the delivery site, is capable of delivering large and/or heavy molecule drugs, is a more effective bactericidal, and is arranged to be safely, simply and reliably operated for self-treatment by an average person in normal home use, even for extended periods of several days at a time. Furthermore, it is contemplated in the practice of the invention that electrical impedance at the administration site on the patient can be substantially reduced to vastly improve permeability and penetration and thereby further enhance medicament delivery.

Basically, the present invention is directed to a new and improved system for iontophoretic drug administration which includes conducting direct electrical current through the skin of a body, and periodically reversing the electrical current and conducting the current through the skin in the opposite direction, to effectively deliver very low frequency AC current, substantially in the critical range of approximately 0.0027 Hz to 10 Hz. It has been discovered that, within this substantially critical frequency window between approximately six minutes per full cycle and approximately ten cycles per second, a dramatic cancellation of skin damaging ions takes place. At frequencies higher than approximately 10 Hz, no substantial effective delivery takes place. At frequencies lower than approximately 0.0027 Hz, the risk of skin injury increases substantially.

It is well known that the positive iontophoretic electrode, in addition to its primary function of driving like polarity ionic substances into the skin of a subject, unfortunately produces skin damaging hydrochloric acid as well. Likewise, the negative iontophoretic electrode, in addition to its primary function of driving like polarity ionic substances into the skin, unfortunately also produces skin damaging sodium hydroxide. However, within the aforestated frequency range of the present invention, either driving polarity delivers the desired ionic therapeutic substances, but also cancels the undesired skin damaging ions with the reverse portion of the electrical cycle. The reason for neutralization of the harsh injury producing chemicals, i.e., hydrochloric acid and sodium hydroxide, is that both of these chemicals require a finite period of time on the skin to cause damage. Hence, these damaging chemicals are made to cancel each other before damage takes place, by critical frequency selection, in accordance with the invention, of the AC driving signal. Therefore, optimization of a long sought therapeutic device with reduced side effects has been achieved.

In accordance with the invention, electronic circuitry is provided to automatically impose the reversal of electrical current at regularly repeating intervals of time, in accordance with the aforedescribed substantially critical frequency range, and the system can be adjusted to conduct the iontophoretic treatment at any desired level of electrical current.

More specifically, the present invention is directed to a novel concept in overcoming the unwanted ions generated at the negative and positive electrodes of an iontophoretic drug delivery system, that lead to skin damage among other undesirable effects during iontophoresis. In attempting to replicate the drug delivery capability of an IV unit that would be used continuously over days, iontophoretic devices of the past are generally unsatisfactory because of their impracticality, complexity and/or the substantial skin damage they would cause. When the demand is for use over days, the new, simplified and improved technology of the present invention is required to overcome the skin damaging acid and alkali generated at the electrodes. This new technology that results in the hydrochloric acid and the sodium hydroxide canceling each other, was achieved with the aforementioned extremely low frequency alternating electrical current that mimics the drug delivery of a direct current system because it is so slow, but deposits otherwise harmful ions on the same skin area to offset or neutralize each other before skin damage can take place.

In accordance with the invention, a basic AC generator delivers a drug into the skin of a patient, but neutralizes opposing harmful chemicals that are inherently developed at the output electrodes when in an aqueous solution or gel form in contact with the skin during electrical current flow. It has been discovered that, when the electrical current is reversed at the slow rate of approximately 0.0027 Hz to 10 Hz, the behavior of the drug is to react as if it were a DC signal in that the polarity at any given moment will drive a like polarity drug component into the skin. The benefit achieved is that the unwanted chemical that was generated at the electrode was neutralized when the signal polarity reversed and developed an opposing chemical to cancel each other at the skin interface.

This non-invasive, minimal side effects system, in accordance with the invention, is designed to deliver drugs either systemically, locally or both, and is also appropriate for other iontophoretic treatment, such as sweat inhibition and the like. It can be made in two or more forms, i.e., a long lasting iontophoretic patch with self-contained electronics, or a larger unit that contains an electronics package for power and control and which terminates into output jacks. The user then plugs an electrical extension cable into these jacks and applies the other end of the cable, which terminates in a remote applicator housing suitable iontophoretic electrodes and drug reservoirs, to the patient. This larger, more powerful unit is generally intended for shorter term use. Large units, employing the frequency range of the present invention, may also be used for treating areas such as the foot which may soak in a liquid surfactant combined with an antifungal agent or the like.

Previous DC iontophoretic devices necessarily required an "inactive" or ground return electrode to electrically complete the circuit. Often, this electrode was remotely connected ("distal" electrode) adding to an unwieldy, space devouring component. Even if the inactive electrode were adjacent to the active, drug driving electrode, it normally occupied at least fifty percent of the space of the device for its simple, one dimensional purpose—to complete an electrical circuit. With the AC system of the present invention, the so-called "inactive" electrode is made active, in that it contributes to driving the drug into the skin when its alternating polarity changes to be the same polarity of the therapeutic medicament. Hence, both electrodes are used to infuse therapeutic drugs into the patient. This has another advantage from the practitioner's view. The polarity of the drug need no longer be known in order to place it in the correct polarity drug reservoir, since the polarity of each reservoir reverses regularly. Otherwise an error could be made. The practitioner also need not stock applicators with two different capabilities—one for positive and one for negative. In effect, the applicator size is doubled because of the presence of the AC signal in accordance with the invention.

The system of the present invention also uses relatively inexpensive silicone/carbon electrodes. While this material is in common use with TENS devices (Transcutaneous Electrical Nerve Stimulators), it is not used for both electrodes for common DC iontophoretic devices. This is because these non-metallic electrodes typically show a high resistance after short use, with a consequent substantial drop in load current (especially the positive electrode). With a slow AC signal, it has been discovered that this build-up of resistance does not take place and both electrodes maintain the desired low electrical resistance. The alternative to these low cost electrodes would be pure and extremely expensive palladium, platinum or rhodium electrodes to minimize corrosion, but with the consequent possibility of metal ions being driven into the skin and further adding to "clutter".

The presence of hydrochloric acid and sodium hydroxide does have a beneficial value in that these chemicals have a bactericidal effect. Each of these chemicals kill different groups of bacteria. In the conventional DC device, only one chemical is present at one electrode and, therefore, attacks only a particular group of microbes. With an AC signal, in accordance with the present invention, the antibacterial effect takes place against the groups of microbes effected by both polarities and, within the substantially critical frequency range of the invention, also avoids damage to the skin.

Heretofore, it was commonly accepted that drugs delivered by iontophoretic systems necessarily had to be limited to approximately one to two percent concentration. Increasing the concentration of the drug not only would not show an increase in drug concentration in the skin, but could actually decrease the amount of drug delivered because of "clutter" and competition to enter a very minute passageway (the eccrine duct). With the slow AC signal of the present invention, drug concentration can now be increased substantially beyond two percent with very important benefits that include enhanced therapeutic value and shortened treatment time.

The reason that the slow AC signal facilitates increased drug dosage or concentration above two percent is as follows: If, for instance, a positively charged drug was in the drug reservoir when the positive half of the AC signal was driving that same reservoir, then the positive component of the drug would be repelled and driven into the skin. Since all drug molecules also contain a negative component that, in this instance, would be left behind in the reservoir (in a DC device) as nonproductive "clutter", when the AC signal swings negative on the other half of the signal, the negative component also will be driven to the skin, thereby eliminating the aforedescribed "clutter" from the reservoir. This "cleansing" of the area, by removal of otherwise delivery inhibiting clutter, enables increased drug concentrations.

A further feature of the present invention resides in the ability to deliver drugs embodying large and/or heavy molecular structures, such as insulin, since the frequency of operation of the system of the present invention both removes "clutter" as a drug transfer impediment and also provides adequate molecular transport times.

In a presently preferred embodiment, the control signal generated by the system of the present invention is usually equal and opposite in all respects so that opposing unwanted chemicals cancel each other and maintain a neutral pH of approximately 7. The electrical circuitry may also be modified to favor the positive portion of the electrical cycle, rather than being exactly the same amplitude as the negative portion of the cycle. Since the skin is naturally acidic at approximately 5.6 pH, the amplitude of the positive signal would be adjusted upward to provide the pH more compatible with the skin. Of course, the opposite effect could be obtained, whenever desired, by increasing the amplitude of the negative portion of the electrical cycle relative to the positive portion.

It may be desirable to maintain a neutral pH of a drug for drug stability, permeability and irritation control among other reasons. In monopolarity DC iontophoretic devices where extremes of acid or alkaline are generated at the electrodes, the drug would quickly reach either extreme. Using an AC signal, in accordance with the invention, with substantially equal and opposite half cycles, both in amplitude and duration, would, as previously indicated, make the pH at the drug delivery site essentially neutral. However, there may be circumstances where it is desirable to controllably alter the pH from neutral. By adjusting the zero reference line, or electrical bias, of the aforedescribed symmetrical AC signal up or down (by switch), the positive signal can be increased or decreased in amplitude relative to the negative signal and vice versa, and, therefore, raise or lower the pH relative to neutral. Ancillary chemicals that are commonly included in drug formulations, such as buffers and isotonic drugs should be dropped from an iontophoretic drug formulation to further reduce clutter.

Modern treatment often demands the simultaneous infusion of different drugs. This is known as multitherapy and is typically performed by inserting two catheters from two different IV units containing different medications to treat multiple problems within one patient. With a non-invasive (no catheter) iontophoretic patch, this is easily accomplished with the two reservoir system utilized by the simplified, more economical and reliable construction and method of the present invention, by placing a different drug into each reservoir. The drugs may be of the same or opposite polarity. The economy of one unit offering two distinct treatments is obvious.

In addition, since both electrodes are "active" with the arrangement of the present invention, the system can deliver twice the amount of drug compared to a comparable DC iontophoretic device. For example, if the drug to be delivered is positive and the signal in one drug reservoir were positive at any given instant, then that reservoir will deliver the drug to the skin. Simultaneously, the other reservoir will be negative and the same drug will ordinarily not flow. However, if a negative "carrier drug" is made part of the formulation, then this carrier drug would flow on the negative half of the electrical cycle while pulling along the desired positively charged active drug. Thus, even though the desired drug is polarity sensitive, the system of the present invention will double the amount of drug delivered. Another embodiment utilizing the same concept is to employ an amphoteric (dipole) surfactant as part of the drug formulation. Not only does the drug flow continuously, but flow rate efficiency is very substantially enhanced because of the permeation qualities of the surfactant.

In addition to the foregoing features, the practice of the present invention may also include the preparatory process of infusing an ionic surfactant, either amphoteric or cationic, at the drug delivery site to lower load resistance by increasing permeability and penetration, and thereby enable higher levels of electrical current and drug delivery with relatively lower driving voltage. This process increases the permeability of the skin, especially the palms and soles. Electrically driving in the surfactant at the delivery site is much more effective than any presoak or swabbing.

Hence, those concerned with development and use of iontophoretic systems in the medical field have long recognized the need for a convenient and effective method and apparatus for preventing skin injury and the formation of vesicles and bulla on the skin in an area subjected to an iontophoretic treatment over extended periods of continuous treatment, which can be physically packaged in a compact and economical configuration, can deliver therapeutic drugs to deeper levels of penetration at a high rate and at higher concentrations, without the need for buffering agents, are capable of delivering large and/or heavy molecular substances, can deliver a plurality of drugs of the same or different polarity simultaneously, and can be used to control pH at the drug administration site.

These and other objects and advantages of the invention will become more readily apparent from the following more detailed description of the invention, when taken in conjunction with the accompanying drawings of illustrative embodiments.

DESCRIPTION OF THE PREFERRED EMBODIMENT(S)

Figure 1:
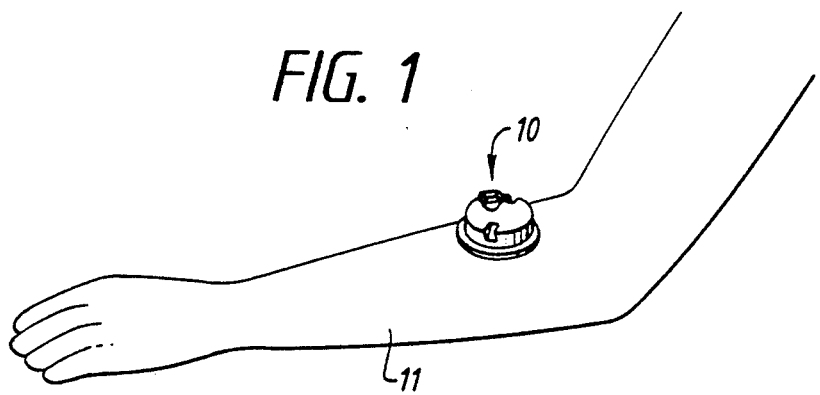
FIG. 1 illustrates an iontophoretic patch administration device constructed in accordance with the invention, and shown installed upon the arm of a human subject.

Referring now to the drawings, and more particularly to FIG. 1, there is shown an iontophoretic patch administration device 10, of relatively simple, economical, reliable and compact construction, embodying features of the present invention, and shown installed upon the arm 11 of a suitable biological subject so that the patch contacts the skin of the subject for appropriate administration of therapeutic treatment by iontophoretic delivery of medicaments or the like.

While the device 10 is shown in its presently preferred embodiment as a compact patch, it will be appreciated by those of ordinary skill in the art that a larger structural and/or physical packaging unit (not shown) may be utilized, including a terminal electrode applicator for contact with the skin, and also embodying various features of the present invention.

Figure 2:
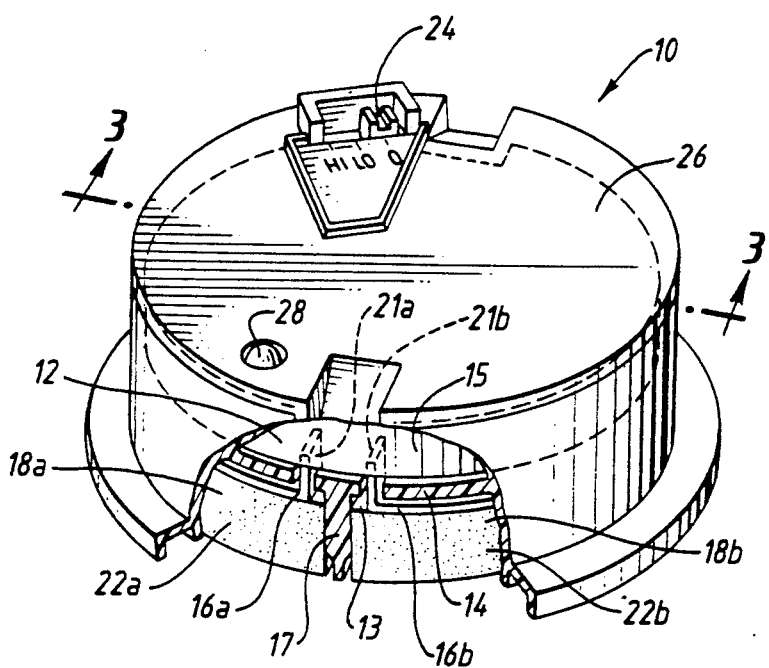
FIG. 2 is an enlarged, perspective view of a presently preferred embodiment of an iontophoretic patch constructed in accordance with the invention, portions being broken away to illustrate internal structure.
Figure 3:
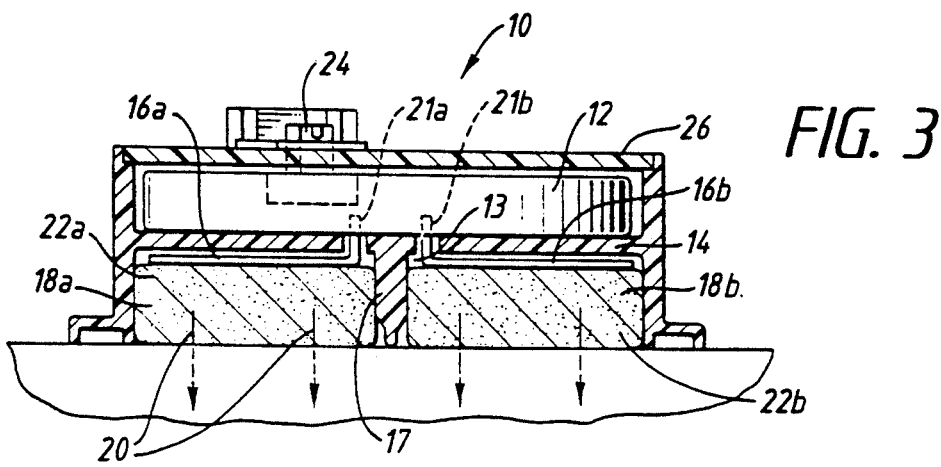
FIG. 3 is a sectional view, taken substantially along the line 3—3 in FIG. 2.

As best observed in FIGS. 2 and 3 of the drawings, the iontophoretic patch 10 is a very compact, circular, cylindrical device fabricated primarily of an outer plastic shell with internal, preferably integrally molded, baffles. The plastic shell and baffles are typically molded of an electrically insulating, flexible vinyl material or the like.

The internal baffles divide the interior of the iontophoretic patch 10 (to be marketed under the trademark LECTRO PATCH by General Medical Company of Los Angeles, Calif.) into upper and lower, hollow internal chambers 12 and 13, respectively, more specifically, by means of an interior baffle member 14. The upper chamber 12 contains a compact electronics package 15, including a suitable microchip and battery power supply. This upper chamber 12 is electrically insulated from the lower chamber 13 by the plastic baffle member 14.

The lower chamber 13 contains a pair of iontophoretic electrodes, 16a and 16b, typically of electrically conductive silicone/carbon material, and which are separated from each other by an electrically non-conductive plastic divider baffle 17 forming a separator wall which divides the lower compartment 13 into a pair of semi-circular electrode chambers and reservoirs 18a and 18b. The chambers 18a and 18b house the electrodes 16a, 16b and contain the therapeutic substances to be ultimately infused into the biological subject, the drug infusion path being indicated generally by the arrows 20 in FIG. 3.

The iontophoretic electrodes 16a, 16b are suitably connected electrically into the electronics package 15 via electrically conductive tabs 21a and 21b, respectively, extending through appropriate slotted openings in the chamber dividing baffle member 14. The silicone/carbon electrodes 16a, 16b are typically fabricated of 1-2 ohm per square centimeter conductive plastic material. While the electrodes 16a, 16b are preferably of silicone/carbon in a presently preferred embodiment of the invention, they may be fabricated of other electrically conductive, non-corrosive materials as well. With the AC signal used in the system of the present invention, there is little or no resistance build-up in the silicone/carbon electrodes.

The drug reservoirs 18a and 18b are filled either with a gel containing the therapeutic substances to be administered or a pair of felt pads 22a and 22b which have been appropriately saturated with the substances to be dispensed.

In addition, an electrical slide switch 24, allowing selection of dosage, schedule and treatment duration, projects physically, for access by an operator, through an upper plastic cover plate 26 adhered to the top of the outer shell of the iontophoretic device 10. The switch 24 is electrically connected in the chamber 12 to the electronics package 15. The switch 24 may be selectively moved between a "0" (off) position, to either a "LO" (low current or lower rate of drug delivery) or "HI" (high current or higher rate of drug delivery) switch positions, to either turn the device 10 "off" so as to cease electrical operation, or to set the device for either high or low electric current rate operation which can remain in such a state on the patient, continuously if desired, for typically either 7 days or 10 days, respectively.

The function of the switch 24 in FIG. 1 with markings "0" (meaning off), "LO" and "HI" is as follows:

1) The "0" position keeps the device from functioning. It may also be used to schedule an "off" interval after leaving one of the other drug delivery positions.

2) The "LO" treatment position infuses the drug at the lowest current level at a continuous, controlled rate. This position can be used for drugs with a narrow therapeutic index for low level infusion. Another use for this position could be a drug with a long half-life with a schedule of intermittent "0" positions to avoid an accumulation that might otherwise result in toxicity.

3) The "HI" treatment position of the switch 24 infuses the drug at a current level typically twice as high as the "LO" setting. This position may be used to maintain efficacy for drugs with a short half-life, such as peptides. Also, the "HI" position can be used for a bolus dose coming off the "LO" position, when therapeutically indicated.

If desired, a second switch (not shown), similar to the slide switch 24, may also be provided and similarly disposed to project through the cover plate 26 of the outer shell of the iontophoretic device 10 and, likewise, be connected to the internal electronics package 15, to selectively vary the frequency of the low frequency duty cycle of operation of the iontophoretic patch 10, as where different size molecules are to be infused into the patient. In this regard, varying frequencies would be used for separation of heavier molecules, such as insulin and the like, to allow for increased drug transport times during the portion of the electrical duty cycle where the particular molecule is delivered from the drug reservoirs 18a, 18b into the skin of the subject being treated. If desired, the electrical system may be modified, in a manner well known to those of ordinary skill in the art, to automatically vary the signal frequency periodically.

In addition, a third switch (also not shown) similar to the switch 24 may be used, in the manner to be subsequently described in connection with the more detailed description of the iontophoretic control system and circuitry, to vary the ratio of the amplitude of the forward to reverse portions of the overall low frequency AC electrical duty cycle, for purposes of controlling the effective pH at the surface, e.g. the skin, of the patient for a variety of medical reasons.

An LED test indicator 28 extends from the electronics package chamber 13 below the cover plate 26, through an appropriate opening in the cover plate, and is observable from the top of the iontophoretic patch 10 to confirm proper electrical operation of the system for the user. An additional switch, such as a membrane switch located inside the patch 10 below the cover plate 26, and operable by pressure on the flexible cover plate, (not shown) may be included to selectively connect the indicator 28 into and out of the electrical circuit, so as to minimize power drain when the indicator is not needed.

Of course, as previously indicated, the invention is not limited to being physically packaged as a patch 10. A larger electronics package may be housed in a remote instrument containing the electronics package, and either battery or plug-in electrical power may be utilized. A local applicator would then be electrically connected by cable to the remote instrument. The applicator would house suitable iontophoretic electrodes and drug reservoirs akin to the chamber 13 of the patch 10 in FIGS. 1–3.

Figure 4:
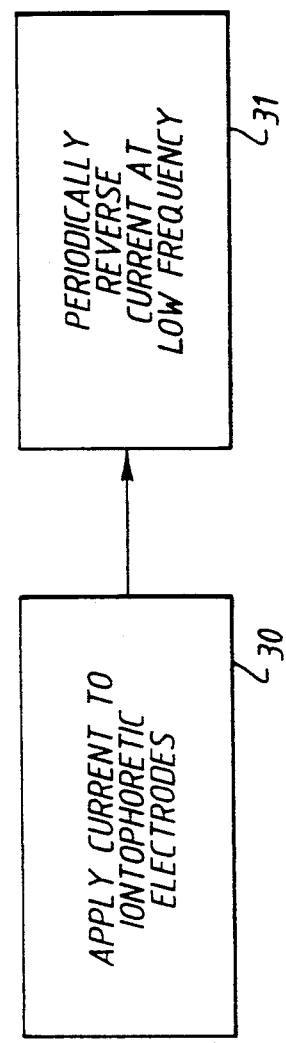
FIG. 4 is a flow chart illustrating a process embodying features of the present invention.

Referring now to FIG. 4 of the drawings, the overall process which facilitates the numerous advantages of the present invention is broadly illustrated and defined. In this regard, the process calls for the step 30 of applying electrical current to a pair of iontophoretic electrodes, such as the electrodes 16a and 16b in the iontophoretic patch 10 illustrated in FIGS. 1–3. The electrical polarity and, therefore, the direction of the electrical current flowing from the electrodes and through the patient is then, in step 31, periodically reversed (twice per AC cycle) at low frequencies in the substantially critical range of approximately 10 Hz to once every three minutes, or a low frequency limit of approximately 0.0027 Hz, to achieve the plethora of advantages previously and subsequently described herein in connection with the practice of the present invention. In the practice of the invention, using lidocaine, the system is optimally operated between one cycle per minute and one cycle every six minutes, with one cycle every two minutes being typical.

Figure 5:
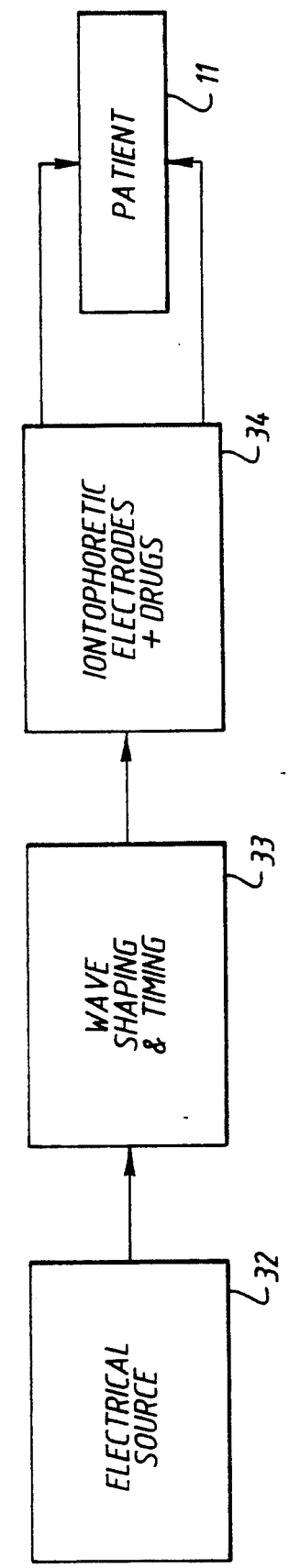
FIG. 5 is a flow chart illustrating a more expanded process in accordance with the invention.

FIG. 5 is a basic block diagram illustrating the invention, wherein an electrical source 32 is directed to appropriate waveshaping and timing circuitry 33 for generating the aforedescribed low frequency AC duty cycle which is then directed as electrical current to iontophoretic electrodes 34 to administer drugs to the patient 11 which is the electrical load in the system. The system illustrated in FIG. 5 may be implemented, in a presently preferred embodiment of the invention, by the more detailed system shown in FIG. 6 of the drawings.

Figure 6:
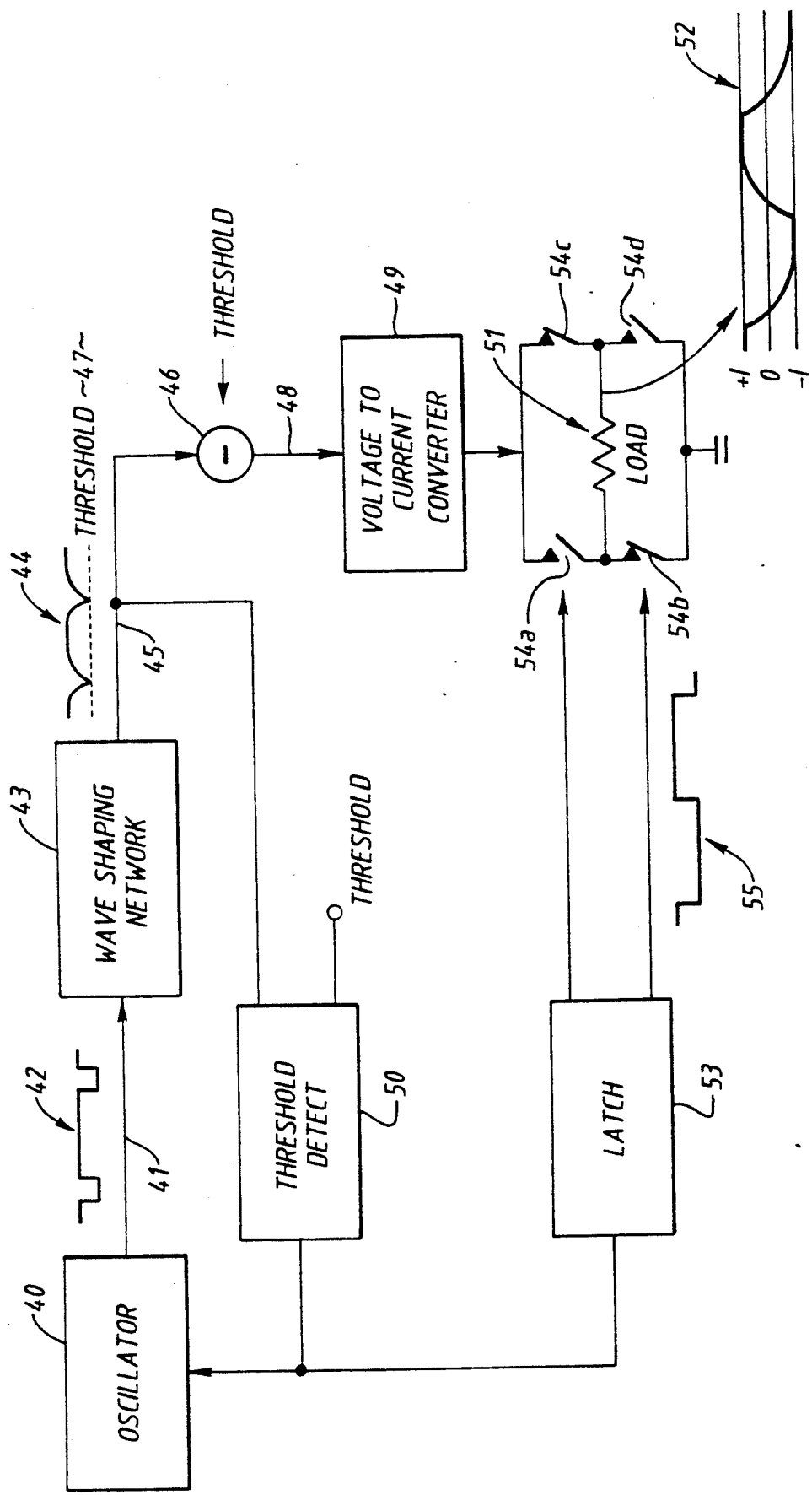
FIG. 6 is a combined overall block diagram and electrical schematic, including waveforms, of a presently preferred iontophoretic administration system embodying features of the present invention.

Referring now more particularly to FIG. 6 of the drawings, there is shown a presently preferred embodiment of an overall system for providing a regulated and periodically reversible electrical current into a variable load resistance (the patient), the electrical current reversing polarity and direction of flow periodically at a very low frequency. In the embodiment shown in FIG. 6, a smooth transition without discontinuity in slope, is made between polarities, thus avoiding a shock sensation to the patient when reversing the electrical current. The magnitude and duty cycle of the positive and negative currents are substantially the same. The system of FIG. 6 utilizes a conventional DC power supply.

In FIG. 6, the timing of current reversals is determined by an oscillator 40, which produces at its output 41 sharp transitions between two levels, as illustrated by the waveform 42. The electrical output 41 is applied to a waveshaping network 43 to produce gradual electrical transitions, as shown by the output waveform 44 available on line 45. The electrical output of the oscillator 40, and thus the sense of the smoothed waveform, is reversed when the waveform crosses a predetermined threshold 47 determined at junction 46 under the control of a threshold detection subsystem 50. The voltage waveform 44, less the threshold 47, is applied over line 48 to a suitable voltage-to-current converter subsystem 49.

The polarity of the electrical current through a floating load 51 (e.g. the patient) reverses at the threshold crossing time, when the instantaneous electrical load current is zero, as illustrated by the waveform 52 in FIG. 6. A latch subsystem 53 controls a plurality of switches 54a–54d, as shown by the waveform 55, to maintain this polarity until the next threshold crossing, producing smooth transitions between electrical current levels which are, by design, substantially equal in magnitude but opposite in sign. The relatively slow rise and decay evident from leading and trailing edges of the waveform 52 provides the desirable electrical ramping up and down of each half cycle to minimize shock sensations.

One example of specific electrical circuitry, suitable for implementing the system shown in FIG. 6, is set forth in Appendix A attached hereto and which is specifically incorporated by reference herein.

With the slow AC signal utilized in the system of the present invention, drug concentration can now be increased substantially beyond two percent with very important benefits that include enhanced therapeutic value and shortened treatment time. The reason for this is, if, for instance, a positively charged drug is in the drug reservoir when the positive half of the AC signal is driving that same reservoir, then the positive component of the drug is repelled and driven into the skin. Since all drug molecules also contain a negative component, that negative component would normally be left behind in the reservoir as non-productive "clutter". However, when the AC signal swings negative on the other half of the signal, the negative component will then also be driven into the skin, thereby eliminating "clutter" from the reservoir. This "cleansing" of the area, by removal of otherwise delivery inhibiting "clutter", enables substantially increased drug concentrations.

It may be desirable to maintain a neutral pH of a drug for drug stability, permeability and irritation control among other reasons. In monopolarity DC iontophoretic devices where extremes of acid or alkaline are generated at the electrodes, the drug would quickly reach either extreme. Using an AC signal, in accordance with the invention, with substantially equal and opposite half cycles, both in amplitude and duration, would make the pH at the drug delivery site essentially neutral. However, as previously indicated, there may be circumstances where it is desirable to controllably alter the pH from neutral. By adjusting the zero reference line, or electrical bias, of the aforedescribed symmetrical AC signal up or down (by switch), the positive signal can be increased or decreased in amplitude relative to the negative signal and vice versa, and, therefore, raise or lower the pH relative to neutral. Ancillary chemicals that are commonly included in drug formulations, but should be dropped from an iontophoretic drug formulation, are buffers and isotonic drugs.

Introducing a positive or negative bias into the waveform 52 in FIG. 6 consists of adding a separate DC current of appropriate polarity through the load 51. This bias current cannot be added directly to the alternating current whose waveform 52 is shown in FIG. 6, because it, too, would then alternate. One example of specific electrical circuitry, suitable for modifying the electrical system shown in FIG. 6 and implemented by the electrical circuitry of Appendix A, is shown in Appendix B which is also attached hereto and is specifically incorporated by reference to form part of the present description. By shifting the amplitude of the electrical current during one portion of the duty cycle relative to the other portion of the duty cycle, pH balance is also shifted and this provides an effective method for controlling the pH at the drug delivery site in the patient.

In addition, since both electrodes are "active" with the simplified arrangement of the present invention, the system can deliver twice the amount of drug compared to a comparable DC iontophoretic device. For example, if the drug to be delivered is negative and the signal in one drug reservoir were negative at any given instant, then that reservoir will deliver the drug to the skin. Simultaneously, the other reservoir will be positive and the same drug will ordinarily not flow. However, if a positive "carrier drug" is included as part of the drug formulation, then this carrier drug would flow on the positive half of the cycle while pulling along the desired negatively charged active drug as well. A typical "carrier drug" would be 4% lidocaine hydrochloride. Hence, even though the desired drug is polarity sensitive, the arrangement described above will double the amount of drug delivered. As will subsequently be explained herein, the "carrier" medium may also be an ionic surfactant, and preferably an amphoteric surfactant.

The iontophoretic electric patch 10 of the present invention is capable of infusing a broad range of drugs up to and including some of the large molecular peptides. This non-invasive system offers increased efficacy with little or no side effects compared to traditional administrative methods. Generally, drugs formulated for iontophoretic delivery should be ionized either negatively or positively, free of causing local irritation or a high rate of hypersensitivity, and have an absence of isotonic and buffer drugs. Used as directed, the iontophoretic patch 10, or the larger version system with a remote applicator, in accordance with the present invention, produces a systemic result as well as a localized effect at the point of application.

The presence of hydrochloric acid and sodium hydroxide also has a beneficial value in that these chemicals have a bactericidal effect. Each of these chemicals kill different groups of bacteria. In the conventional DC device, only one chemical is present at one electrode and, therefore, attacks only a particular group of microbes. With an AC signal, operating in the critical low frequency range in accordance with the present invention, the antibacterial effect takes place against the groups of microbes effected by both polarities, all without damage to the skin and the drug delivery site.

Another application of the AC signal to sterilize is to send this signal down conductive catheter tubes. Infection of the wound that the catheter enters is of major concern and a common problem with dialysis users, IV patients, etc.

As previously suggested, unique features of the iontophoretic patch 10 of the present invention include: no tissue damage, rapid onset of action, long term dosing at selected levels, compatibility with either polarity drug, capability for delivery of two separate drugs at the same time (multitherapy) and ability to deliver higher drug concentration. These and other features of the iontophoretic patch 10 greatly enhance drug therapy. Operating ease comes through the selection switch 24 to provide programmed input. Selection assures consistent dosing within the general population, thereby maintaining effective plasma concentrations.

Figure 7:
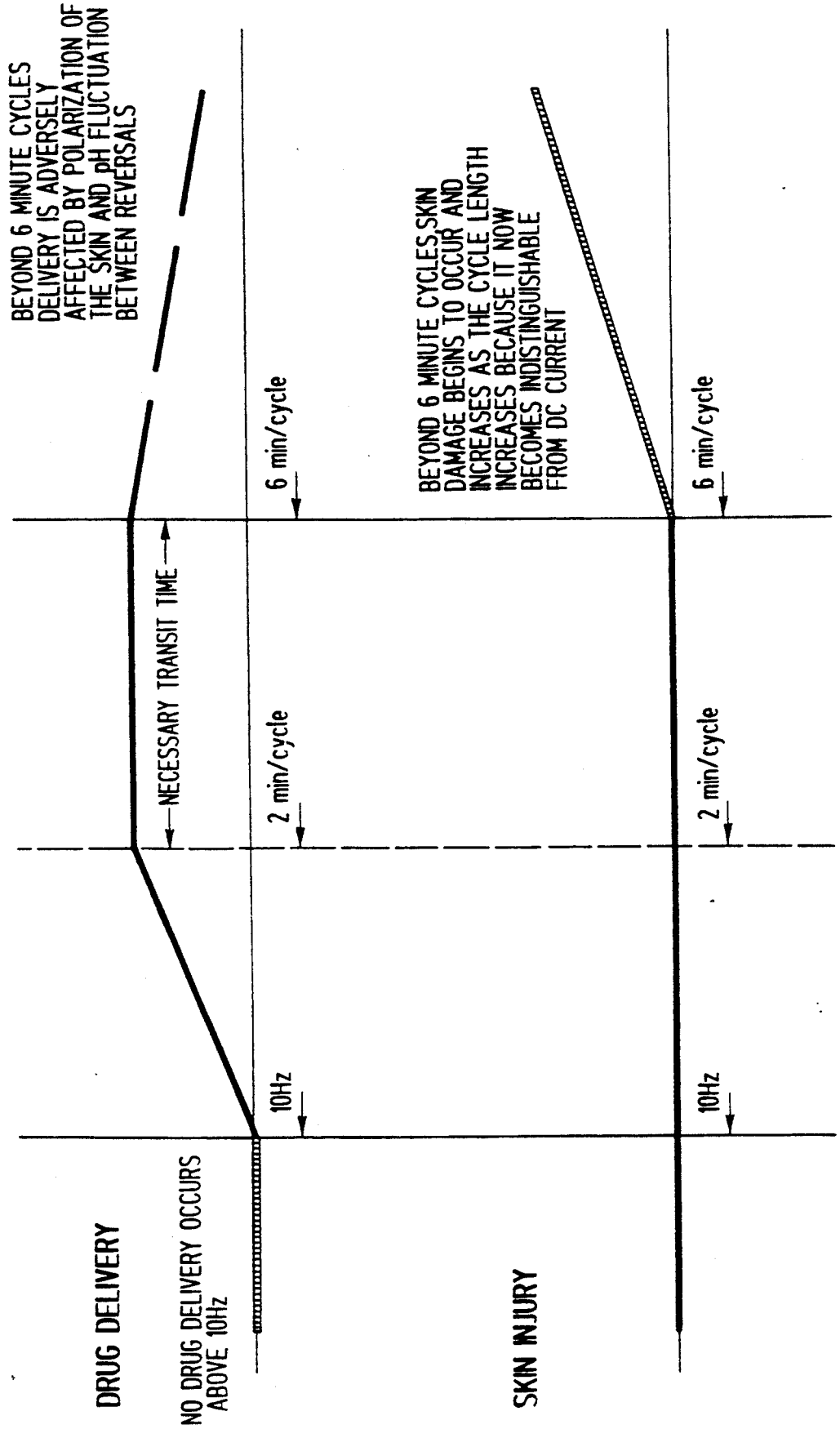
FIG. 7 is a graphical representation illustrating the appropriate frequency window for simultaneous drug delivery and prevention of skin injury.

Referring now more particularly to FIG. 7 of the drawings, there is shown, in graphical form, an illustration of the manner in which drug delivery and skin injury typically vary over the substantially critical frequency window between approximately six minutes per full cycle and approximately ten cycles per second. In this frequency range, there is a dramatic cancellation of skin damaging ions. At frequencies higher than approximately 10 Hz, no substantial effective drug delivery takes place, and other factors such as skin polarization and pH fluctuation may typically reduce drug delivery beyond six minutes per full cycle. At frequencies lower than six minutes per cycle, or approximately 0.0027 Hz, the risk of skin injury increases substantially.

The iontophoretic patch 10 of the present invention is capable of delivering drugs at a continuous, controlled rate. This allows the physician/pharmaceutical manufacturer to titrate drug dosage to the most effective concentration with minimum or no side effects. Significantly elevated concentrations can be obtained in 60 minutes or less after start of treatment. Thus, a steady-state concentration of the drug can be maintained during the dosing interval. The physician specifies the duration of application and has a variety of treatment regimens from which to select.

In addition to the treatment regimens previously described, and solely by way of example and not by way of limitation, other possible regimens may include: A scheduled switching regimen between "LO" and "HI" positions of the switch 24 for a wide therapeutic index drug, to avoid building a tolerance to a fixed, static level. Another therapeutic opportunity may be where multi-therapy is indicated with drugs of similar halflives. This application would allow total drug separation (one drug in each of the reservoirs 18a, 18b of the patch 10), for infusion of drugs of the same polarity (alternate delivery) or opposite polarity (simultaneous delivery). Still another therapeutic variation could be to halve the infused dosage (intermittent dosing) in the "LO" position of the switch 24 by filling only one reservoir with the drug of choice and the other reservoir with common tap water. Conversely, drug delivery can be doubled if a compatible "carrier" drug of opposite polarity to the active drug is included in the reservoirs. When the signal reverses, so as to now block transport of the active drug, the oppositely charged carrier drug would flow with the piggy-backed active drug.

The iontophoretic patch 10, in accordance with the invention, is designed to infuse either positively or negatively charged drugs at a constant rate, by way of example in connection with a presently preferred embodiment of the invention, for up to seven days in the "HI" position of the switch 24 or ten days in the "LO" position. The clinician fills a hypodermic syringe with approximately 6 cc of the appropriate drug and then proceeds to fully saturate both felt pads 22a, 22b in each drug reservoir 18a, 18b, respectively. Care must be taken to avoid wetting the bottom of the wall 17 separating the reservoirs 18a, 18b and that the pads 22a, 22b are slightly above this separator wall (see FIG. 3) and recessed within the housing before application to the skin of a patient. Pad fibers must not cross over this separator wall 17 because they may otherwise cause the device to malfunction.

Suitable skin preparation must precede iontophoretic patch surface adhesion. One possibility is to prepare application areas by swabbing with approximately fifty percent isopropyl alcohol. At higher concentrations, permeability is decreased due to the precipitation of tissue proteins.

Iontophoretic treatment should preferably be preceded by a skin preparation process that strongly enhances permeability. It has long been a desire in iontophoretic drug delivery to infuse drugs anywhere on the human body. Penetrating the palms of the hands or the soles of the feet is virtually impossible because the skin in these areas is about forty times thicker than other areas of the body. Additionally, other areas of the body, as well as differences in skin resistance among different human beings, often limits the sites for infusion. This is especially true when using the low power of an iontophoretic patch 10 as compared to the relative high power of a full-sized instrument where five times or more voltage could be available to overcome high skin resistance. It is, therefore, a great advantage to be able to treat any area without having to be selective.

Historically, the art calls for preparing the skin with alcohol, acetone or surfactants by swabbing the area to be treated with these chemicals to remove oils and other debris to enhance electrical contact for the iontophoretic applicator. Obviously, these traditional methods of skin preparation were not satisfactory in overcoming the limits of drug delivery to many parts of the body. There have also been some efforts to enhance delivery of metallic ions by means of an anionic surfactant, as well as in vitro experiments to deliver certain drugs using an anionic surfactant.

In accordance with the invention, it has been discovered that using an appropriate ionic surfactant and driving the surfactant into the skin with the iontophoretic device (or an equivalent current source), prior to drug delivery, greatly lowers skin resistance and increases skin permeability thereby allowing treatment to take place anywhere on the human body. An alternate arrangement could allow the ionic surfactant to be included in the treatment drug formulation where compatible. Forms of the ionic surfactant can be liquid, gel or equivalent. Suitable ionic type classifications for such surfactants would be cationic and amphoteric. Amphoteric surfactants appear to work best only with an AC signal, such as that used in the system of the present invention. With cationic monopolarized surfactants, both AC and DC signals work. In this regard, the amphoteric surfactant can be the "carrier" medium for another drug to be delivered.

The use of amphoteric and cationic surfactants, electrically delivered into the treatment site, to enhance permeability and penetration at the site, can be effectively utilized as a skin preparation technique for both iontophoretic and non-iontophoretic drug delivery at that site.

In the practice of the present invention, it has been discovered that amphoteric surfactants performed much more efficiently than cationic surfactants, while cationic surfactants were considerably more effective than anionic surfactants such as sodium lauryl sulfate. Suitable examples of such surfactants successfully utilized in the practice of the invention are:

| SURFACTANT PREPARATION SOLUTIONS | |
|---|---|
| (1) AMPHOTERIC | |
| Product Name: | AMPHOTERIC-L |
| Chemical Name: | COCO AMIDOPROPYL BETAINE |
| Physical Appearance: | Clear Liquid |
| Manufacturer: | Exxon Chemical Company Performance Products Group Tomah Products 1012 Terra Drive (P.O. Box 388) Milton, Wisconsin 53563 |
| (2) CATIONIC | |
| Product Name: | DEHYQUART A |
| Chemical Name: | CETYL TRIMETHYL AMMONIUM CHLORIDE |
| Physical Appearance: | Clear Liquid |
| Manufacturer: | Henkel Corporation Chemical Specialties Division 300 Brookside Avenue Ambler, Pennsylvania 19002 |

Surfactants may include suitable functional materials such as coupling agents, antimicrobials, chelating agents and the like.

Of course, it will be appreciated that the aforementioned ionic surfactants are presented only by way of example, and those of ordinary skill in the art may substitute other amphoteric or cationic surfactants, currently known or unknown, without departing from the spirit and scope of the invention.

The vastly increased permeability and penetration capability at the treatment site, made possible by use of an appropriate ionic surfactant, and particularly an amphoteric surfactant, yields yet another embodiment of the invention relating to sweat control by iontophoresis. In this regard, sacrificial aluminum electrodes may be substituted for the silicone/carbon electrodes 16a, 16b, to direct ions into the eccrine duct for sweat control.

The aluminum ions precipitate the skin protein therefore causing a plug that lasts weeks (no sweat period). The treatment site is either first prepared using an appropriate surfactant, as outlined above. Thereafter, tap water is placed in the reservoirs 18a, 18b. Alternatively, an appropriate ionic, and preferably amphoteric, surfactant is placed into the reservoirs 18a, 18b adjacent the aluminum electrodes for delivery into the treatment site.

In general, placement for systemic infusion is the volar surface of the forearm near the elbow. If the use is to treat a lesion or any other specific site, the patch 10 should be placed over that site for target delivery. If the application site is contoured, the iontophoretic patch 10 may be bent to conform with this irregular surface. The bend should take place in line with the separation wall 17 running down the center of the patch 10.

In normal operation, the switch 24 is moved from the "0" position to either "LO" or "HI" as prescribed. The user may feel a gentle tingle for only the first approximately thirty seconds to one hour (priming period) of treatment, depending to some extent upon the permeability at the delivery site. Treatment is then continued for the prescribed period of time. The patch 10 is switched to the "0" position when not in use.

After completion of treatment, the iontophoretic patch 10 should normally be discarded. The hands and drug application site should be washed with soap and water and then dried to remove any remnant drug.

In normal use, after the patch 10 has been applied and working for approximately one hour, the following procedures can be used throughout the seven day ("HI") or ten day ("LO") treatment to prove workability. If the green indicator 28 lights when switched into the electrical circuitry (in accordance with the circuitry of Appendix A), it means the batteries are fresh and the device is delivering the medication. If the indicator 28 fails to light, it means that the batteries are dead and the device must be replaced. If the green indicator 28 flashes on and off continuously, it can mean one of the following malfunctions: a) that the drug is leaking from one side of the separation wall 17 to the other (oversaturation of pads), b) that the drug level is too low and more must be added to the felt pad 18a or 18b, or that the patch 10 itself is not firmly adhered to the skin surface (especially a contoured surface) and c) (for investigators) that an unproven formulation is non-ionic or of such poor conductivity that minimum current needs for the "LO" position (approximately 0.5 ma by way of example) or the "HI" position (approximately 1.0 ma by way of example) cannot be met. Under these conditions, the investigator may consider adding another drug to act as a "carrier" for the substantially non-ionic drug. Electroosmotic transport of water or solvent also enhances penetration of non-electrolytes.

It will be apparent that the various electrical subsystems indicated in FIGS. 5 and 6 of the drawings can be implemented readily by those of ordinary skill in the art without the exercise of inventive skill.

Hence, those concerned with development and use of iontophoretic systems in the medical field have long recognized the need for a convenient and effective apparatus and method for preventing iontophoretic burns and irritation and the formation of vesicles and bulla on the skin in an area subjected to an iontophoretic treatment over extended periods of continuous treatment, which can be physically packaged in a simple, reliable, relatively inexpensive and compact configuration, can increase permeability and penetration at the treatment site, can deliver therapeutic drugs at a high rate and at higher concentrations, without the need for buffering agents, are capable of delivering large molecular substances, can deliver a plurality of drugs of the same or different polarity simultaneously, and can be used to control pH at the drug administration site.

Accordingly, it will be apparent from the foregoing that, while particular forms of the invention have been illustrated and described, various modifications can be made without departing from the spirit and scope of the invention. Therefore, it is not intended that the invention be limited, except as by the appended claims.

I claim:

1. A method of applying iontophoretic treatment to a biological subject, said method including the steps of:
   conducting an electrical current through a surface of said subject in a first direction from a first electrode to a second electrode on said subject; and
   intermittently reversing, at a relatively low frequency which prevents skin damage, between approximately 20 times per second and approximately once every three minutes, the polarity of said electrodes to cause said electrical current to flow in a second direction opposite to said first direction, whereby iontophoretic treatment may be continuous for extended periods of time.

2. A method as set forth in claim 1, including the step of:
   selectively varying the amplitude of the electrical current in one direction relative to the amplitude of the electrical current in the opposite direction to control pH at the surface of said subject.

3. A method as set forth in claim 1, including the step of:
   selectively varying the frequency of the electrical current to accommodate the transport times of different size molecules.

4. A method as set forth in claim 1, wherein multiple drugs are delivered.

5. A method as set forth in claims 1 or 4, wherein drugs of the opposite polarity are delivered simultaneously.

6. A method as set forth in claim 1 or 4, wherein drugs of the same polarity are driven alternately from different electrodes.

7. A method as set forth in claim 1, wherein a carrier of opposite polarity is added to a drug to be driven by at least one of said electrodes.

8. A method of clearing ionic clutter from an iontophoretic drug administration system, said method including the steps of:
   conducting an electrical current through a surface of a subject being treated, in a first direction from a first electrode to a second electrode on said subject; and
   periodically reversing, at a relatively low frequency which avoids damage to said subject, between approximately 20 times per second and approximately once every three minutes, the polarity of said electrodes to cause said electrical current to flow in a second direction opposite to said first direction, whereby the resulting very low frequency alternating current eliminates ionic clutter and facilitate continuous drug administration for extended periods of time.

9. A method of iontophoretic infusion of medical substances into a biological subject, comprising the steps of:

locating a pair of electrically conductive electrodes adjacent to a surface of said subject to be treated;

placing at least one medical substance between at least one of said electrodes and said surface of said subject to be treated;

conducting an electrical current through said surface of said subject in a first direction from a first of said electrodes to a second of said electrodes on said subject; and periodically and regularly reversing, at a relatively low frequency, between approximately 20 times per second and approximately once every three minutes, the polarity of said electrodes to cause said electrical current to flow in a second direction opposite to said first direction, whereby skin damage to said subject is avoided and drug infusion may be continuous for extended periods of time.

10. A method as set forth in claim 9, including the step of:

selectively varying the amplitude of the electrical current in one direction relative to the amplitude of the electrical current in the opposite direction to control pH at the surface of said subject.

11. A method as set forth in claim 9, including the step of:

selectively varying the frequency of the electrical current to accommodate the transport times of different size molecules.

12. A method as set forth in claim 9, wherein multiple medical substances are delivered.

13. A method as set forth in claims 9 or 12, wherein medical substances of the opposite polarity are delivered simultaneously.

14. A method as set forth in claims 9 or 12, wherein medical substances of the same polarity are driven alternately from different electrodes into said surface.

15. A method as set forth in claim 9, wherein a carrier substance of opposite polarity is added to a medical substance to be driven by at least one of said electrodes.

16. A method as set forth in claim 9, including the additional step of:

iontophoretically delivering a surfactant material into said surface to lower electrical resistance and enhance drug penetration.

17. A method as set forth in claim 9, including the additional step of:

iontophoretically delivering an amphoteric surfactant material into said surface to lower electrical resistance and enhance drug penetration.

18. A method as set forth in claim 9, including the additional step of:

iontophoretically delivering a cationic surfactant material into said surface to lower electrical resistance and enhance drug penetration.

19. A method of iontophoretic infusion of medical substances into a biological subject, comprising the steps of:

locating a pair of electrically conductive electrodes upon said subject to be treated;

placing at least one medical substance between at least one of said electrodes and a surface of said subject to be treated;

conducting an electrical current through said surface of said subject in a first direction from a first of said electrodes to a second of said electrodes on said subject; and intermittently reversing the polarity of said electrodes to cause said current to flow in a second direction opposite to said first direction, at a relatively low frequency which prevents skin damage to said subject and simultaneously provides adequate molecular transport time for said medical substance to be delivered into said surface of said subject, whereby infusion of said medical substance may be continuous for extended periods of time and wherein the polarity reversal occurs after the accumulated time periods of actual substantial electrical current flow in either direction equal a selected period of time between approximately 0.05 seconds and approximately 3 minutes.

* * * * *